United States Patent [19]

Moghe et al.

[11] Patent Number: 5,597,556
[45] Date of Patent: Jan. 28, 1997

[54] COLORED BICARBONATE CONTAINING SOLID COMPOSITION

[75] Inventors: Bhalchandra Moghe, Edison; Makarand Shevade, Plainsboro; Radhakrishna Kasat, Bellemead; Elizabeth Linn, North Arlington, all of N.J.

[73] Assignee: The Mennen Company, Morristown, N.J.

[21] Appl. No.: 425,926

[22] Filed: Apr. 20, 1995

[51] Int. Cl.$^6$ ........................................... A61K 7/32
[52] U.S. Cl. .......................... 424/65; 424/76.1; 510/158
[58] Field of Search ................. 424/65, 76.1; 252/123

[56] References Cited

U.S. PATENT DOCUMENTS

| | | | |
|---|---|---|---|
| 3,914,405 | 10/1975 | Shepherd et al. | 424/49 |
| 3,983,060 | 9/1976 | Dill | 260/29.6 RW |
| 4,292,035 | 9/1981 | Battrell | 8/137 |
| 4,382,079 | 5/1983 | Marschner | 424/65 |
| 4,414,200 | 11/1983 | Murphy et al. | 424/63 |
| 4,440,741 | 4/1984 | Marschner | 424/65 |
| 4,440,742 | 4/1984 | Marschner | 424/65 |
| 4,524,062 | 6/1985 | Laba et al. | 424/65 |
| 4,659,571 | 4/1987 | Laba | 424/65 |
| 4,664,909 | 5/1987 | Marschner | 424/65 |
| 4,721,581 | 1/1988 | Ramachandran et al. | 252/135 |
| 4,759,924 | 7/1988 | Luebbe | 424/42 |
| 4,761,248 | 8/1988 | Clift | 252/527 |
| 4,801,445 | 1/1989 | Fukui et al. | 424/69 |
| 4,814,165 | 3/1989 | Berg et al. | 424/63 |

FOREIGN PATENT DOCUMENTS 116406   1/1988   European Pat. Off. .

*Primary Examiner*—C. Warren Ivy
*Assistant Examiner*—Evelyn Huang
*Attorney, Agent, or Firm*—Antonelli, Terry, Stout & Kraus

[57] ABSTRACT

A colored, soap-gelled composition, comprising an alcohol, a soap in an amount effective to gel the composition, an alkali metal bicarbonate, and an inorganic pigment. Whereas alkali metal bicarbonate deodorant compositions colored with FD & C or D & C colorants do not exhibit stable color for extended periods of time, the compositions of the present invention, using inorganic pigments, exhibit stable color for extended periods, even under accelerated, e.g., high temperature, conditions.

35 Claims, No Drawings

COLORED BICARBONATE CONTAINING SOLID COMPOSITION

BACKGROUND OF THE INVENTION

The present invention relates to a colored, soap-containing, solid composition, e.g., a deodorant composition or, more particularly, a deodorant stick composition, containing an alcohol, gelled with a soap, an alkali metal bicarbonate and a pigment, wherein the composition maintains a stable color over an extended period of time.

Bicarbonate containing solid compositions based on alcoholic soap gels are known in the prior art. U.S. Pat. Nos. 4,382,079; 4,440,741 and 4,440,742 to Marschner (the contents of each of which are incorporated herein by reference) describe deodorant cosmetic sticks containing an alkali metal bicarbonate dispersed or dissolved in aqueous or anhydrous polyhydric alcohol or a mixture of polyhydric and monohydric alcohol, gelled by a minor amount of an alkali metal salt of a fatty acid. While it is known in the art to make such deodorant sticks uncolored or to include FD & C or D & C colorants, applicants have found that solid soap-gelled, bicarbonate containing compositions colored using FD & C and D & C colors are unstable over extended periods of time. Accordingly, it is still desired to provide a bicarbonate-containing soap-gelled solid composition which can maintain a stable, aesthetically, superior color for a relatively long period of time.

SUMMARY OF THE INVENTION

Accordingly, it is an object of the present invention to provide a colored, soap-containing, solid composition including an alkali metal bicarbonate, the color of which remains stable for an extended period of time.

It is a further object of the present invention to provide a colored, soap-containing solid deodorant composition including an effective amount of a deodorant active metal bicarbonate, the color of which remains stable over an extended period of time.

It is a further object of the present invention to provide a colored deodorant stick composition containing a soap gelling agent and an effective amount of a deodorant active alkali metal bicarbonate, the color of which remains stable of an extended period of time.

The foregoing objects are achieved by providing a composition comprising an alcohol, a soap gelling agent, an alkali metal bicarbonate and at least one inorganic pigment. Since the alkali metal bicarbonate, e.g., sodium bicarbonate and/or potassium bicarbonate, is a deodorant active material, the composition is a deodorant composition when a deodorant effective amount of alkali metal bicarbonate is added. The composition can be made into a bar (e.g., soap bar) or stick (deodorant stick) form. The use of inorganic pigments results in a composition which does not exhibit a color change over an extended period of time, even under accelerated (e.g., high temperature) conditions. Examples of inorganic pigments include bismuth oxychloride, mica, iron oxides, titanium dioxide, manganese violet, ultramarine blue, ultramarine pink, ultramarine violet, ultramarine rose, chromium hydroxide green, chromium oxide green, bronze powder, aluminum powder, ferric ferrocyanide, ferric ammonium ferrocyanide and disodium copper EDTA.

Illustratively, the soap used to gel the composition is a salt, preferably a sodium salt, of fatty acids for example, sodium salts of saturated or unsaturated fatty acids having a carbon chain length of $C_{12}$–$C_{22}$. Most preferably, the soap gellant is an alkali metal stearate, e.g., sodium stearate. The alkali metal stearate and alkali metal bicarbonate may be separately added to the remaining elements of the composition to form the composition or may be formed in situ by reaction between alkali metal carbonate and stearic acid.

The pigment is preferably contained in the composition in an amount of 0.01 to 5% by weight, more preferably 0.01 to 1% by weight, most preferably 0.01 to 0.2% by weight. The alkali metal bicarbonate is preferably contained in the composition in an amount of 0.01 to 5% by weight, more preferably 0.01 to 3% by weight, most preferably 0.01 to 1% by weight.

DETAILED DESCRIPTION OF THE INVENTION

While the invention will be described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present specification, where compositions are described as including or comprising specific components or materials, it is contemplated by the inventors that compositions of the present invention also consist essentially of, or consist of, the recited components or materials. Accordingly, throughout the present disclosure any described composition of the present invention can consist essentially of, or consist of, the recited components or materials.

The present invention contemplates a colored, soap-containing solid composition (e.g., a deodorant composition or deodorant stick composition) containing alcohol and, optionally water, an alkali metal bicarbonate, and gelled with soaps, e.g., salts of saturated or unsaturated fatty acids, the color being provided by an inorganic pigment.

The alcohol included in the solid composition of the present invention can be a monohydric and/or polyhydric alcohol (for example, ethanol as a monohydric alcohol, and propylene glycol and dipropylene glycol as polyhydric alcohol). The alcohol can be a mixture of alcohols, including a mixture of monohydric and polyhydric alcohols, or a mixture of monohydric alcohols or a mixture of polyhydric alcohols. Various polyhydric alcohols which can be used in soap-gelled alcohol and water-containing stick compositions are described in U.S. Pat. No. 4,759,924 to Luebbe et al, the contents of which are incorporated herein by reference in their entirety, and can also be used in the present invention.

A necessary component of the composition according to the present invention is a soap gel-forming agent. Sodium salts of fatty acids of carbon chain length $C_{12}$–$C_{22}$, e.g., sodium salts of saturated fatty acids having the above-mentioned carbon chain length, can be utilized as the gel-forming agent. Preferred gel-forming agents according to the present invention include sodium salts (that is, soaps) of relatively long-length-carbon-chain saturated fatty acids (for example, sodium salts of saturated fatty acids having carbon chain lengths of $C_{20}$–$C_{22}$). The fatty acid portions of the soap can include a mixture of different saturated fatty acids of carbon chain length in the range of $C_{12}$–$C_{22}$, preferably including some $C_{20}$ and $C_{22}$. By utilizing such relatively long chain length fatty acids, a product is provided having a relatively high melting temperature, and, correspondingly, relatively greater stability.

The alkali metal bicarbonate is preferably sodium bicarbonate and/or potassium bicarbonate, most preferably sodium bicarbonate. The alkali metal bicarbonate is preferably contained in the composition in an amount of 0.01 to 5% by weight, more preferably 0.01 to 3% by weight, most preferably 0.01 to 1% by weight. In this connection 3% is the solubility limit of baking soda in water. Thus, if the quantity of bicarbonate is greater than 3%, the composition becomes more opaque. The bicarbonate can be itself added with the other elements to form the composition or may be formed in situ by the reaction of stearic acid with an alkali metal carbonate.

The inorganic pigment may be, for example, at least one of bismuth oxychloride, mica, iron oxides, titanium dioxide, manganese violet, ultramarine blue, ultramarine pink, ultramarine violet, ultramarine rose, chromium hydroxide green, chromium oxide green, bronze powder, aluminum powder, ferric ferrocyanide, ferric ammonium ferrocyanide and disodium copper EDTA. The ultramarine are complexes of sodium aluminum sulfosilicates having the typical formula Na(AlSiO)S with C.I. 77013. Chromium oxide green has the formula $Cr_2O_3$ with C.I. Index No. 77288 and C.I. Pigment Green No. 17. Chromium hydroxide Green has the formula $Cr_2O(OH_4)$ with C.I. Index No. 77289 and C.I. Pigment Green No. 18. The inorganic pigment is contained in the composition in an amount sufficient to provide the composition with color. While inorganic pigments are currently used in commercially available cosmetic products such as blush, eye shadow, eye mascara, etc., these compositions contain pigments in a larger amount than do the compositions of the present invention. The amount of pigment contained in products such as blush, eye shadow, eye mascara, etc. is high enough to deposit the color when the composition is applied to the skin. The pigment content in the compositions of the present invention are much lower such that when, for example, deodorant is applied to the skin, the skin is not colored by the composition. Preferably, the pigment is contained in the composition in an amount of 0.01 to 5% by weight, more preferably 0.01 to 1% by weight, most preferably 0.01 to 0.2% by weight.

The pigment is dispersed (suspended) in the composition. Preferably, the pigment has a particle size of 40 μm or less.

Illustratively, and not limiting, the composition according to the present invention can also include the following amounts (in percent by weight of the total weight of the composition) of other components:

Alcohol (e.g., propylene glycol): 55–80%

Water: 9–25%

Soap: 4–10%

Other materials can be included in the compositions according to the present invention, and include various cosmetically active materials. Thus, materials such as other deodorant active materials (including fragrances), sunscreens, skin conditions, nail conditioners, and the like, can be included in the composition, provided that they do not unsatisfactorily affect color and, where appropriate, can be applied to the human body.

Compositions according to the present invention have use as bar soap or underarm deodorant compositions (e.g., by application to axillary regions of the human body), since the alkali metal bicarbonate is a deodorant active material. Various other deodorant active materials can be included in compositions according to the present invention and are described in U.S. Pat. No. 4,759,924, and include bacteriostats and fragrances (e.g., perfumes), and bactericides, among others. For example, another deodorant material useful in the present compositions in addition to the bicarbonate is 2-4-4'-trichloro-2'-hydroxydiphenyl ether (CTFA name: Triclosan).

The compositions according to the present invention are manufactured by processing techniques conventional in the art. Specifically, the solid components of the composition (other than the bicarbonate) are melted and then the components are mixed. Preferably, the inorganic pigment is added after addition of the bicarbonate. Preferably, the fragrance (if any) is added last, with the previously mixed components being cooled to a lower temperature (while still maintaining a liquid) prior to adding the fragrance, so as to limit any volatilization of the fragrance. While still in the liquid state, the composition is filled in a dispensing package (as conventional in the art) and then cooled to solidify the product in the package.

Alternatively, a portion or all of the soap gellant and/or alkali metal bicarbonate can be produced in situ by mixing the components, including stearic acid and alkali metal carbonate so as to produce, in situ, alkali metal stearate and alkali metal bicarbonate.

The compositions according to the present invention are utilized by conventional techniques. For example, when utilizing compositions according to the present invention as an axillary deodorant solid stick, the solid stick product is elevated out of a dispensing package so as to expose the stick product, and the exposed portion of the stick product is then rubbed against, e.g., the axillary region of the human body so as to deposit the deodorant active materials in the axillary region.

While in the foregoing the present invention has been described in terms of a deodorant solid stick composition for use in axillary regions, the present invention is not so limited, and the composition according to the present invention has various uses depending on the active material incorporated therein, including as a soap or deodorant for other parts of the body, sunscreen, insect repellant, etc.

In the following, specific examples of compositions within the scope of the present invention will be set forth. Of course, these specific examples are illustrative of the present invention and are not limiting.

In the following examples, the stated percentages are percentages by weight, of the stated component, relative to the total weight of the composition. The names utilized are the CTFA names for the ingredients, where applicable.

COMPARATIVE EXAMPLE AND EXAMPLES II–IV

Five compositions were prepared having the components (with amounts in weight percent) indicated in the following table. It will be recognized that FD & C green was used as a colorant in the Comparative Example while inorganic pigments (chrome oxide green and chrome hydroxide green) were used as the colorant in Examples I to IV. A portion of each of the resulting compositions was stored at room temperature for more than six months and the color change observed after approximately twelve weeks and after six months. Another portion of each of the compositions was stored at 120° F. for four weeks and the color change observed. As can be seen from the following table, a color change was observed in the comparative example containing FD & C green at room temperature after about twelve weeks and at 120° F. after about four weeks. On the other hand, the compositions of the present invention exhibited a stable color for an extended period of time both at room temperature (greater than six months) and at 120° F. (more than four weeks).

|  | Comparative Example | Examples | | | |
| --- | --- | --- | --- | --- | --- |
|  |  | I | II | III | IV |
| Propylene Glycol | 68.47 | 70.47 | 70.47 | 71.17 | 71.17 |
| Irgasan DP 300 | 0.25 | 0.25 | 0.25 | 0.25 | 0.25 |
| Sodium Stearate | 7.00 | 7.00 | 7.00 | 7.00 | 7.00 |
| D.I. Water | 20.48 | 20.48 | 20.48 | 20.48 | 20.48 |
| Stearyl Alcohol | 0.20 | 0.20 | 0.20 | — | — |
| Sodium Chloride | 0.50 | 0.50 | 0.50 | — | — |
| Sodium Bicarbonate | 1.00 | 1.00 | 1.00 | 1.00 | 1.00 |
| FD&C Green (0.1%) | 0.30 | — | — | — | — |
| Chromium Oxide Green | — | 0.10 | — | 0.10 | — |
| Chromium Hydroxide Green | — | — | 0.10 | — | 0.10 |
| Fragrance | Q.S | Q.S | Q.S | Q.S | Q.S |
| Stability |  |  |  |  |  |
| Room Temp. (more than 6 mos.) | Color Change | STABLE | STABLE | STABLE | STABLE |
| 120° F. (4 weeks) | Color Change | STABLE | STABLE | STABLE | STABLE |

Examples V and VI

The compositions shown in the following table were prepared by incorporating the indicated components in the amount indicated in weight percent. The stearic acid in sodium carbonate react in situ to form sodium stearate and sodium bicarbonate.

Baking Soda Containing Deodorant Stick Formula Examples

|  | Example V | Example VI |
| --- | --- | --- |
| Propylene Glycol | 68.87 | 68.00 |
| Irgasan | 0.25 | 0.25 |
| Stearic Acid | 4.00 | 4.00 |
| Sodium Carbonate | 1.60 | 1.60 |
| D.I. Water | Q.S. | Q.S. |
| Sodium Bicarbonate | 1.00 | 1.00 |
| PPG-5 CETETH-20 | 3.00 | 3.00 |
| Fragrance | 2.00 | 1.00 |
| Chromium Oxide Green | — | 0.10 |
| Chromium Hydroxide Green | 0.10 | — |

(Note: The sodium Stearate is produced In situ)

While we have shown and described several embodiments in accordance with the present invention, it is understood that the same is not limited thereto, but is susceptible of numerous changes and modifications as known to those skilled in the art. Therefore, we do not wish to be limited to the details shown and described herein, but intend to cover all such changes and modifications as are encompassed by the scope of the appended claims.

We claim:

1. A colored, soap-gelled composition, comprising: an alcohol; a soap in an amount effective to gel the composition; an alkali metal bicarbonate; and an inorganic pigment.

2. A colored, soap-gelled composition according to claim 1, wherein said composition is a deodorant composition and wherein said alkali metal bicarbonate is contained in a deodorant effective amount.

3. A colored, soap-gelled composition according to claim 2, wherein said deodorant composition is a deodorant stick composition and wherein said soap is contained in an amount effective to provide a solid stick composition.

4. A colored, soap-gelled composition according to claim 1, further comprising water.

5. A colored, soap-gelled composition according to claim 4, wherein said alcohol is contained in an amount of 55–80wt. %, said water is contained in an amount of 9–25 wt. %, said soap is contained in an amount of 4–10 wt. %, said alkali metal bicarbonate is contained in an amount of 0.01–5 wt. %, and said inorganic pigment is contained in an amount of 0.01–5 wt. %.

6. A colored, soap-gelled composition according to claim 5, wherein said alkali metal bicarbonate is contained in an amount of 0.01–3 wt. %.

7. A colored, soap-gelled composition according to claim 5, wherein said alkali metal bicarbonate is contained in an amount of 0.01–1 wt. %.

8. A colored, soap-gelled composition according to claim 5, wherein said inorganic pigment is contained in an amount of 0.01–1 wt. %.

9. A colored, soap-gelled composition according to claim 5, wherein said inorganic pigment is contained in an amount of 0.01–0.2 wt. %.

10. A colored, soap-gelled composition according to claim 2, wherein said inorganic pigment is contained in said composition in an amount effective to provide color to said composition and less than an amount effective to color human skin upon application of said composition thereto.

11. A colored, soap-gelled composition according to claim 1, wherein said inorganic pigment is contained in said composition in an amount of 0.01 to 5 wt. %.

12. A colored, soap-gelled composition according to claim 1, wherein said inorganic pigment is contained in an amount of 0.01–1 wt. %.

13. A colored, soap-gelled composition according to claim 5, wherein said inorganic pigment is contained in an amount of 0.01–0.2 wt. %.

14. A colored, soap-gelled composition according to claim 1, wherein said alcohol is at least one polyhydric alcohol.

15. A colored, soap-gelled composition according to claim 14, wherein said alcohol is at least one alcohol selected from the group consisting of propylene glycol and dipropylene glycol.

16. A colored, soap-gelled composition according to claim 1, wherein said alcohol is at least one monohydric alcohol.

17. A colored, soap-gelled composition according to claim 16, wherein said alcohol is ethanol.

18. A colored, soap-gelled composition according to claim 17, wherein said alcohol comprises a mixture of at least one monohydric alcohol and at least one polyhydric alcohol.

19. A colored, soap-gelled composition according to claim 1, wherein said soap is at least one salt of at least one fatty acid.

20. A colored, soap-gelled composition according to claim 19, wherein said soap is at least one sodium salt of at least one saturated fatty acid having a carbon chain length $C_{12}$–$C_{22}$.

21. A colored, soap-gelled composition according to claim 20, wherein said soap comprises sodium stearate.

22. A colored, soap-gelled composition according to claim 1, wherein said alkali metal bicarbonate is selected from the group consisting of sodium bicarbonate and potassium bicarbonate.

23. A colored, soap-gelled composition according to claim 1, wherein said inorganic pigment is selected from the group consisting of bismuth oxychloride, mica, iron oxides, titanium dioxide, manganese violet, ultramarine blue, ultramarine pink, ultramarine violet, ultramarine rose, chromium hydroxide green, chromium oxide green, bronze powder, aluminum powder, ferric ferrocyanide, ferric ammonium ferrocyanide and disodium copper EDTA.

24. A colored, soap-gelled composition according to claim 23, wherein said inorganic pigment is selected from the group consisting of chromium oxide green, chromium hydroxide green and ultramarines.

25. A colored, soap-gelled composition according to claim 1, wherein said inorganic pigment is dispersed in said composition and has a particle size of 40 μm or less.

26. A colored, soap-gelled deodorant composition, comprising:
   55–80 wt. % of at least one alcohol selected from the group consisting of ethanol, propylene glycol and dipropylene glycol;
   9–25 wt. % water;
   4–10 wt. % of at least one salt of a fatty acid;
   0.01–5 wt. % of at least alkali metal bicarbonate selected from the group consisting of sodium bicarbonate and potassium bicarbonate; and
   0.01–5 wt. % of at least one inorganic pigment selected from the group consisting of bismuth oxychloride, mica, iron oxides, titanium dioxide, manganese violet, ultramarine blue, ultramarine pink, ultramarine violet, ultramarine rose, chromium hydroxide green, chromium oxide green, bronze powder, aluminum powder, ferric ferrocyanide, ferric ammonium ferrocyanide and disodium copper EDTA.

27. A colored, soap-gelled composition according to claim 26, wherein said at least one inorganic pigment is selected from the group consisting of chromium hydroxide green and chromium oxide green.

28. A colored, soap-gelled deodorant composition according to claim 27, wherein said inorganic pigment is contained in said composition in an amount of 0.01 to 1 wt. %.

29. A colored, soap-gelled composition according to claim 27, wherein said inorganic pigment is contained in an amount of 0.01 to 0.2 wt. %.

30. A colored, soap-gelled composition according to claim 23, wherein said at least one inorganic pigment is selected from the group consisting of chromium hydroxide green and chromium oxide green.

31. A colored, soap-gelled composition according to claim 30, wherein said inorganic pigment is contained in an amount of 0.01 to 5 wt. %.

32. A colored, soap-gelled deodorant composition according to claim 30, wherein said inorganic pigment is contained in said composition in an amount of 0.01 to 1 wt. %.

33. A colored, soap-gelled composition according to claim 30, wherein said inorganic pigment is contained in an amount of 0.01 to 0.2 wt. %.

34. A colored, soap-gelled composition prepared by mixing an alcohol, a soap in an amount effective to gel the compositions, an alkali metal bicarbonate, and an inorganic pigment.

35. A colored, soap-gelled deodorant composition prepared by mixing:
   55–80 wt. % of at least one alcohol selected from the group consisting of ethanol, propylene glycol and dipropylene glycol;
   9–25 wt. % water;
   4–10 wt. % of at least one salt of a fatty acid;
   0.01–5 wt. % of at least alkali metal bicarbonate selected from the group consisting of sodium bicarbonate and potassium bicarbonate; and
   0.01–5 wt. % of at least one inorganic pigment selected from the group consisting of bismuth oxychloride, mica, iron oxides, titanium dioxide, manganese violet, ultramarine blue, ultramarine pink, ultramarine violet, ultramarine rose, chromium hydroxide green, chromium oxide green, bronze powder, aluminum powder, ferric ferrocyanide, ferric ammonium ferrocyanide and disodium copper EDTA.

* * * * *